United States Patent [19]

Orr

[11] 4,163,447
[45] Aug. 7, 1979

[54] HEARTBEAT RATE MONITOR

[76] Inventor: Thomas Orr, Starboard House, 30 Shore Rd., Warsash, Southampton, England

[21] Appl. No.: 873,977

[22] Filed: Jan. 31, 1978

[30] Foreign Application Priority Data

Feb. 11, 1977 [GB] United Kingdom ............... 5746/77

[51] Int. Cl.² ............................................. A61B 5/02
[52] U.S. Cl. ..................................... 128/666; 128/690
[58] Field of Search ....................... 128/2.05 P, 2.05 T, 128/2.05 B, 2.06 F, 2.1 A, 2.1 P

[56] References Cited

U.S. PATENT DOCUMENTS

| 3,769,974 | 11/1973 | Smart et al. | 128/2.05 P |
| 3,807,388 | 4/1974 | Orr et al. | 128/2.05 T |
| 3,835,837 | 9/1974 | Peek | 128/2.05 P |
| 3,937,004 | 2/1976 | Natori | 128/2.05 T |
| 3,993,047 | 11/1976 | Peek | 128/2.05 P |
| 4,063,551 | 12/1977 | Sweeney | 128/2.05 P |

Primary Examiner—William E. Kamm
Attorney, Agent, or Firm—Mason, Fenwick & Lawrence

[57] ABSTRACT

A heartbeat rate monitor has a light source, powered by a rechargeable battery, for transilluminating skin tissue. A semiconductor detector which produces an output signal in dependence on light originating from the light source and reflected from the skin tissue, and hence on changes in arterial blood flow, is additionally used, on exposure to ambient light, to produce a current for recharging the battery.

9 Claims, 6 Drawing Figures

HEARTBEAT RATE MONITOR

BACKGROUND OF THE INVENTION

1. Field of the Invention

This invention relates to heartbeat rate monitors.

2. Cross-reference to Related Patents

U.S. Pat. No. 3,807,388 issued 30 Apr. 1974 and assigned to the present applicant relates to a heartbeat rate monitor. U.S. Pat. application Ser. No. 656,842 filed 9 Feb. 1976 and now allowed, also assigned to the present applicant, relates to a transducer for detecting heartbeats.

3. Description of the Prior Art

It has been proposed, for example in the above-mentioned U.S. Pat. No. 3,807,388, to provide a heartbeat rate monitor and personal pulse indicator in compact form. The monitor may, for example, be incorporated in an electronic watch to be worn on the wrist and incorporate timing circuits whereby signals respectively representing the heartbeat rate and the time of day can be derived and used to energise separate displays, or a single selectively energised display. The electric power requirements of the monitor are supplied by a battery, and this introduces the problem of having to replace the battery at intervals, when it becomes discharged.

SUMMARY OF THE INVENTION

One object of the present invention is to provide a heartbeat rate monitor in which the above-mentioned problem is overcome.

Another object of the present invention is to provide a heartbeat rate monitor in which the electric power requirements are supplied by a rechargeable battery and the battery is recharged with current derived from a semiconductor detector which is also alternatively used to produce a signal in dependence on the heartbeat rate.

According to the present invention therefore there is provided a heartbeat rate monitor comprising a light source for transilluminating skin tissue, a semiconductor detector for detecting variations in the light reflected from the skin tissue so as to produce a signal responsive to and dependent on changes in blood flow, an indicator for giving an indication of the heartbeat rate in dependence on said signal, and a rechargeable electric power source for powering said light source and said indicator, said detector means being capable, on exposure to ambient light, of supplying a current to recharge said source.

The heartbeat rate monitor may be formed as a separate entity in its own housing, but is preferably housed in a watch-type casing, and this may be a wristwatch casing, a pocket watch casing, or the casing of a watch intended to be secured to clothing and of the type commonly worn by nurses. The casing may also house timing means for giving an indication of the time of day. The timing means is preferably electronic and powered by said rechargeable power source. Both the time and the heartbeat rate may be shown digitally, for example, by respective figure-of-8 light emitting diode or liquid crystal display indicators.

The above, and other objects, features and advantages of this invention will be apparent from the following detailed description of illustrative embodiments which is to be read in connection with the accompanying drawings.

DESCRIPTION OF THE PREFERRED EMBODIMENTS

Figure 1:
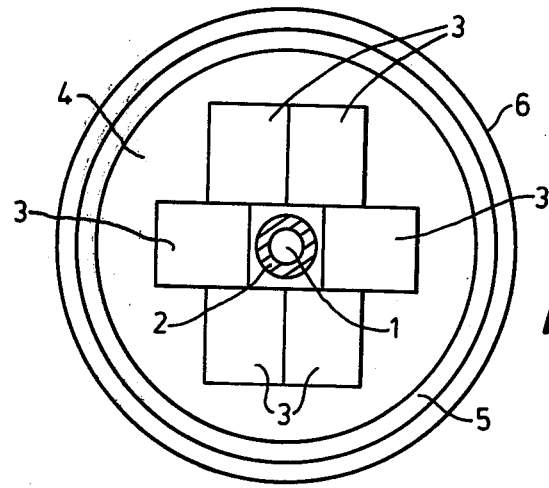
FIG. 1 shows a rear view of a wristwatch casing forming part of a heartbeat rate monitor.

Referring to FIG. 1, a heartbeat rate monitor comprises a light emitting diode 1 surrounded by opaque plastics material 2, and around this are disposed six silicon photodiodes 3 arranged as shown to receive light originating from the light emitting diode, which is reflected from skin tissue of the wearer. The whole is set in transparent plastics material 4 and surrounded by an ambient light shield 5 on the rear of a watch casing 6.

Figure 2:
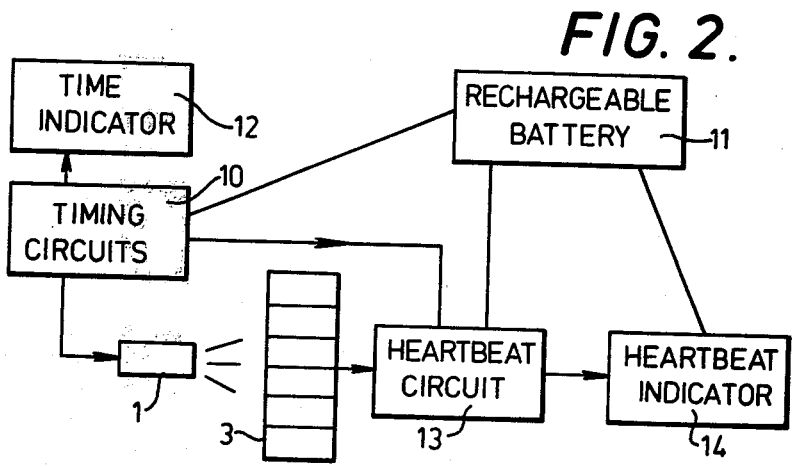
FIG. 2 shows schematically a circuit for heartbeat rate indication.

FIG. 2 shows a timing circuit 10 powered by a rechargeable battery 11 and producing signals to drive a time indicator 12. A pulse signal is also derived from the timing circuit 10 to pulse energise the light emitting diode 1. A signal derived from the photodiodes 3 is processed by a heartbeat circuit 13 to produce an output signal to drive a heartbeat rate indicator 14. The heartbeat circuit 13 and the indicator 14 are also powered by the battery 11.

Figure 3:
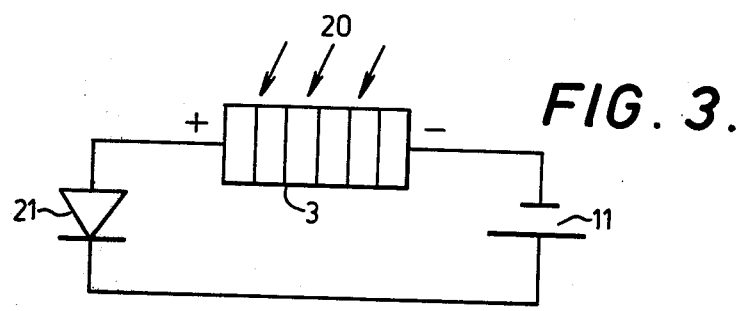
FIG. 3 shows schematically a circuit for battery recharging.

FIG. 3 shows the photodiodes 3 in the batter charging mode when exposed to ambient light 20. The photodiodes 3 are connected in series with a blocking diode 21 and the battery 11.

Human skin is a reasonably good transmitter of visible and near infra-red light and, within the outer layers at least, no changes in transmission or absorption are observed over the short time periods under consideration. However, the inner layers of skin tissue are supplied with blood for their correct functioning, and it is the interaction of this blood with incident light that produces changes in the reflected light level. Skin tissue is supplied with arterial blood from the heart via a complex network of arterioles and capillaries. Arterial blood flows in pulses which decrease in intensity along the arterial circuit, the major drop in pulse pressure occuring before the capillary bed flow stage. Thus the venous blood return circuit can be ignored.

The main arteries are usually deep seated, but the arterioles and capillaries are much closer to the skin surface and are arranged in complex parallel coupled circuits between the arteries and veins.

While the arterioles and capillaries are quite elastic to the blood pulse, it is thought to be certain properties of blood, rather than the movement of vascular walls under the skin surface, that give rise to absorption and hence reflectivity changes. There are two mechanisms which may account for these changes, both are complex and inter-related, and they relate to the volume of a blood pulse within the skin tissue, and the oxygen content of the blood.

Considering these two absorption phenomena together, and assuming that light absorption due to the volume of blood within the arterial pulse wave is the dominant effect, it appears that the use of light within the wavelength range 500 to 600 nm would give rise to the maximum light absorption during the blood pulse. However, there obviously has to be sufficient reflected light from the blood content of the skin tissue to activate the photodiodes 3, and operation of the light emitting diode 1 within the range 600 to 650 nm will produce a lower absolute value of light absorption level, and therefore a higher intensity of reflected light.

A signal change is also produced due to the change in oxygen content of the blood during the arterial pulse, and this will tend to reduce slightly the absorption maximum to be expected during the peak of the arterial pulse, and therefore the amplitude of the signal.

The outer surface of the human skin is known to exhibit a spectrally sensitive transmission factor, but over the range under consideration there are no major changes in transmission levels.

The light emitting diode 1 may therefore emit light of wavelength in the range 500 to 650 nm, and, for the reason outlined above, preferably in the range 600 to 650 nm. The photodiodes 3 preferably comprise silicon, selenium or cadmium sulphide/cuprous sulphide photodiodes. Usually, in order to produce a sufficient output current, a plurality of such photodiodes 3, for example, six as illustrated, will be used connected in parallel with one another. They are preferably disposed to encircle the light emitting diode 1, suitable screening 2 being provided to prevent light passing directly from the light emitting diode 1 to the photodiodes 3. When used to indicate heartbeat rate, the light emitting diode 1 must be positioned in close proximity to the skin tissue and the photodiodes 3 must be arranged to receive reflected light originating from the light emitting diode 1, but not ambient light. This may, for example, be arranged by having the light emitting diode 1 and the photodiodes 3 disposed on the rear surface of a wristwatch casing 6 as illustrated, if necessary with a suitable circumferential seal around the rear surface of the wristwatch casing 6, to prevent the entry of ambient light. The entry of ambient light may also be reduced by using polarising filter means.

In the alternative mode, when the photodiodes 3 are to be used to supply a current to recharge the battery 11, which may for example be a silver oxide or nickel cadmium battery, it is of course essential that the photodiodes 3 are exposed to ambient light. In the case described above, where the photodiodes 3 are on the rear of the wristwatch casing 6, this can be achieved when the watch is removed by exposing the rear to ambient light. The photodiodes 3 can however be mounted on the front surface of the wristwatch casing 6 which would normally be exposed to ambient light, in which case they are shielded from ambient light when a measurement of heartbeat rate is to be taken using the tip of a person's finger or thumb. This can be achieved, for example, by having the light emitting diode 1 and photodiodes 3 arranged in such a way that they are covered and shielded from ambient light by the said tip of a person's finger or thumb, when the person's heartbeat rate is to be measured by transillumination of the skin tissue of that finger or thumb.

For the purpose of providing sufficient electric current to recharge the battery 11, a different interconnection of the photodiodes 3 may be necessary to obtain the required voltage. For example, the photodiodes 3 may need to be connected in series instead of in parallel, and a suitable switching arrangement can be provided to achieve this. Moreover, a blocking diode 21 is connected in series with the photodiodes 3 and the battery 11 to prevent the battery discharging through the photodiodes 3 when in darkness or not otherwise in the charging mode.

The timing circuits 10 may comprise a crystal controlled oscillator and suitable divider circuits to divide the frequency of the signal produced by the oscillator to produce signals to energise the time indicator 12 to give the required indication of time.

Although the light emitting diode 1 may be energised with dc, it is preferable to derive a signal from some suitable point in the divider circuit to provide power for the light emitting diode 1, so that it emits flashes of light at a frequency substantially higher than the highest heartbeat rate to be expected. The flashes may, for example, be at a frequency at 1 kHz. The output signal produced by the photodiodes 3 is then a signal having the same frequency as the flashes of light but amplitude modulated at the heartbeat rate, and by eliminating dc components from this signal the effect of any ambient light falling on the light emitting diode 1 can be reduced.

Figure 4:
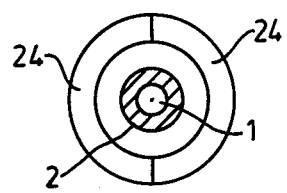
FIGS. 4 and 5 show modifications to the arrangement of FIG. 1.

Various modifications can of course be made. For example, as illustrated in FIG. 4, arcuate shaped and in particular semicircular shaped photodiodes 24 may be disposed around the light emitting diode 1.

Figure 5:
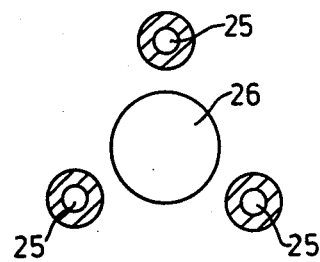

Alternatively, as illustrated in FIG. 5, a plurality, such as three, light emitting diodes 25 may be disposed around a central photodiode means 26 and be cyclically pulse energised. Suitable electronic processing of the resulting output signal from the photodiode means 26 can result in improved discrimination of heartbeats and rejection of interference.

If desired, the time indicator 12 and the heartbeat rate indicator 14 may be combined into a single, selectively-energised indicator. In any case the indicator(s) will normally be a numeric, that is figure-of-8, display preferably using liquid crystal devices or light emitting diodes.

Figure 6:
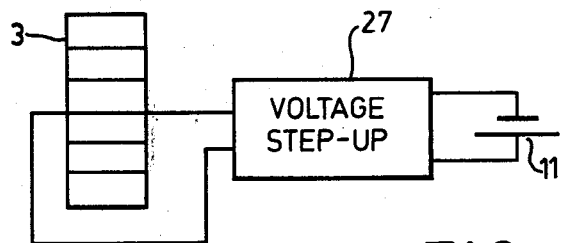
FIG. 6 shows a modification to the arrangement of FIG. 3.

Finally, as illustrated in FIG. 6, the parallel arrangement of the photodiodes 3 may be retained during charging of the battery 11 and the necessary voltage derived by an electronic voltage step-up circuit 27.

Although illustrative embodiments of the invention have been described in detail herein with reference to the accompanying drawings, it is to be understood that the invention is not limited to those precise embodiments, and that various changes and modifications can be effected therein by one skilled in the art without departing from the scope and spirit of the invention as defined by the appended claims.

I claim:
1. A heartbeat rate monitor comprising:
a light source for transilluminating skin tissue;
semiconductor detector means disposed to receive light from said light source reflected from said skin tissue and capable of detecting variations in the level of said light reflected from said skin tissue so as to produce an electric signal responsive to changes in arterial blood flow in said skin tissue, said detector means also being capable, on exposure to ambient light, of supplying a recharging current for a power source;
indicator means for indicating the heartbeat rate in dependence on said electric signal;
means for supplying said electric signal from said detector means to said indicator means;
a rechargeable electric power source;

means to supply said current from said detector means to said power source to recharge said power source; and means to energise said light source from said battery.

2. A body-worn, compact, heartbeat rate monitor comprising:

a watch-type casing;

timing circuit means for producing an electric signal to be used to display the time of day;

display means mounted in said casing for displaying the time of day and energised by said electric signal produced by said timing circuit means;

a light source including at least one light emitting diode mounted in said casing for transmilluminating skin tissue;

semiconductor detector means mounted in said casing adjacent to said light source for detecting variations in the level of light from said light emitting diode reflected from the skin tissue and producing a further electric signal responsive to changes in arterial blood flow in said skin tissue, said detector means also being capable, on exposure to ambient light of supplying a recharging current for a power source;

means for supplying said further electric signal to said display means for giving an indication of the heartbeat rate in dependence on said further electric signal;

a rechargeable electric power source mounted in said casing for energising said timing circuit means, said display means and said light source; and means for supplying said current from said detector means to said power source to recharge said power source.

3. A heartbeat rate monitor according to claim 2 wherein said display means is a numeric light emitting diode display.

4. A heartbeat rate monitor according to claim 2 wherein said display means is a numeric liquid crystal display.

5. A heartbeat rate monitor according to claim 2 wherein said light emitting diode is pulse energised.

6. A heartbeat rate monitor according to claim 2 wherein said light source comprises a plurality of light emitting diodes, and said monitor further comprises means to energise said light emitting diodes cyclically.

7. A heartbeat rate monitor according to claim 2 wherein said semiconductor detector means comprises at least one photodiode.

8. A heartbeat rate monitor according to claim 2 wherein said semiconductor is silicon.

9. A heartbeat rate monitor according to claim 2 wherein said means for supplying said current to recharge said power source includes voltage step-up means.

* * * * *